(12) United States Patent
Chevallet et al.

(10) Patent No.: US 7,115,206 B2
(45) Date of Patent: Oct. 3, 2006

(54) METHOD FOR IN-LINE PREPARATION OF LIQUID FOR AN EXTRACORPOREAL BLOOD TREATMENT APPARATUS

(75) Inventors: Jacques Chevallet, Serezin du Rhone (FR); Guy Mercier, Bron (FR); Laurent Simard, Saint Genis Laval (FR)

(73) Assignee: Gambro Lundia AB, Lund (SE)

( * ) Notice: Subject to any disclaimer, the term of this patent is extended or adjusted under 35 U.S.C. 154(b) by 425 days.

(21) Appl. No.: 10/684,463

(22) Filed: Oct. 15, 2003

(65) Prior Publication Data

US 2004/0079703 A1 Apr. 29, 2004

Related U.S. Application Data

(60) Provisional application No. 60/428,897, filed on Nov. 26, 2002.

(30) Foreign Application Priority Data

Oct. 15, 2002 (FR) .................................. 02 12776

(51) Int. Cl.
*B01D 61/30* (2006.01)
*B01D 61/26* (2006.01)
*B01D 35/12* (2006.01)

(52) U.S. Cl. .................... 210/791; 210/198.1; 210/201; 210/203; 210/232; 210/321.6; 210/321.71; 210/646; 210/650

(58) Field of Classification Search ................ 210/109, 210/143, 198.1, 201, 203, 232, 240, 252, 210/254, 300, 316, 340, 321.6, 321.72, 343, 210/417, 420, 428, 433.1, 767, 791, 646, 210/650, 321.71

See application file for complete search history.

(56) References Cited

U.S. PATENT DOCUMENTS

| 4,702,829 | A |   | 10/1987 | Polaschegg et al. |
| 5,342,518 | A | * | 8/1994 | Posner et al. ................ 210/232 |
| 5,405,528 | A | * | 4/1995 | Selbie et al. ................. 210/232 |
| 5,660,722 | A |   | 8/1997 | Nederlof |
| 5,702,597 | A | * | 12/1997 | Chevallet et al. ......... 210/195.2 |
| 5,846,419 | A |   | 12/1998 | Nederlof |
| 5,895,578 | A | * | 4/1999 | Simard et al. ............... 210/636 |
| 6,039,877 | A | * | 3/2000 | Chevallet et al. ........... 210/636 |
| 6,187,207 | B1 |   | 2/2001 | Brauer |
| 6,303,036 | B1 |   | 10/2001 | Collins et al. |
| 6,740,235 | B1 | * | 5/2004 | Gill ............................. 210/238 |
| 6,926,826 | B1 | * | 8/2005 | Reid ............................ 210/232 |
| 2002/0023865 | A1 | * | 2/2002 | Northcut et al. ............ 210/192 |

* cited by examiner

*Primary Examiner*—John S. Kim
(74) *Attorney, Agent, or Firm*—Finnegan, Henderson, Farabow, Garrett & Dunner, L.L.P.

(57) ABSTRACT

A method for in-line preparation of liquid for an extracorporeal blood treatment apparatus that makes provision for placing a filter in correspondence with each of two successive filtration stations, for carrying out a liquid preparation cycle, for removing the filter, which operates in correspondence with a first filtration station, for placing in correspondence with the first filtration station the filter that operated in correspondence with the second filtration station, for placing a new filter in correspondence with a second filtration station and for launching a new sterile liquid preparation cycle. The invention also provides a device for implementing the described method and an apparatus for extracorporeal blood treatment, which incorporates this device.

15 Claims, 4 Drawing Sheets

METHOD FOR IN-LINE PREPARATION OF LIQUID FOR AN EXTRACORPOREAL BLOOD TREATMENT APPARATUS

CROSS REFERENCE TO RELATED APPLICATIONS

This application claims the priority of French Patent Application No. 02 12776, filed on Oct. 15, 2002, and the benefit of U.S. Provisional Application No. 60/428,897, filed on Nov. 26, 2002, the contents of which are incorporated herein by reference.

FIELD OF THE INVENTION

The present invention relates to a method and a device for the in-line preparation of liquid for an apparatus designed for the extracorporeal blood treatment, and to an apparatus for the treatment of blood using the said method and the said device.

In particular, the invention is applicable to the preparation of the liquid intended for use as an infusion liquid and/or as a dialysis liquid in the treatment substituting for the renal function.

It is known that patients affected by renal insufficiency may undergo a treatment which involves the removal of blood from the patient, the treatment of the blood and the restoration of the treated blood to the same patient.

For this purpose, the blood is normally conveyed in an extracorporeal circuit and is circulated in a first chamber of a treatment unit with a semipermeable membrane.

More specifically, in the dialysis treatment, provision is made to make the blood circulate in a first chamber of a dialyser with two chambers separated by a semipermeable membrane. In the second chamber, a dialysis liquid of suitable chemical composition is made to circulate so as to obtain a transfer by diffusion of the solutes through the membrane.

In contrast, in the haemofiltration treatment, provision is made to extract a portion of plasmatic water through the treatment unit or the haemofilter and simultaneously to perfuse a substitute liquid into the patient in order to partially compensate for the amount of plasmatic water taken through the haemofilter. During the haemofiltration process, migration of the solutes takes place by transport through the semipermeable membrane of the haemofilter.

Finally, haemodiafiltration is a combination of the two treatments which have just been described.

The dialysis liquid and the substitute liquid are liquids having an identical or largely identical chemical composition: they are essentially isotonic and contain the main electrolytes of the blood.

The correct production of such liquids and, in particular, of the substitute liquid which comes into direct contact with the patient's blood is a problem which is currently giving great cause for concern. In particular, in order not to cause discomfort for the patient, it has proved to be important to guarantee the production of substitute liquids and possibly of dialysis liquids which are sterile (that is to say free from living bacteria or micro-organisms) and non-pyrogenic (that is to say free from pyrogenic elements whose introduction into the blood has been held responsible for disorders such as fever, shivering, nausea and anaphylactic reactions).

A technical solution currently adopted by the present applicant provides for the use of three filtration stages: firstly, a filtration phase, for example of normal drinking water, is carried out in order to obtain water with a high degree of purity. Next, the water obtained in this way is sent to the dialysis machine in which a second and a third filtration stage follow each other. In more detail, the second filtration stage provides a filter which is replaced once a month, while the third filtration stage provides a small cartridge and a corresponding line of pipes which are replaced at the end of each treatment.

Although the technical solution described above operates satisfactorily, it involves the use of three filtration stages with three filters different from one another, and it requires the user to carry out vigorous disinfection at the end of each treatment, in particular because of the fact that the second filter is reused over a relatively long period. The cleaning and disinfection between two successive sessions must in particular be executed with extreme care and attention in order not to cause irreversible damage to the membrane of the second filter.

Consequently, one object of the present invention is to propose a method and a device for in-line preparation of liquid, able to use a single type of filter and at the same time to provide a very high degree of sterility of the liquid product, with simplification of the disinfection procedures with successive treatments. Another subject of the invention is an apparatus for extracorporeal blood treatment which uses the said method and the said device.

These objects, and others, which will become apparent during the following description, are mainly achieved with
- a method for the in-line preparation of liquid for an apparatus for extracorporeal blood treatment, which apparatus comprises at least one fluid path 12 from a liquid source to a region 4 for injecting the said liquid into an extracorporeal blood circuit and/or into a cardiovascular system of a patient and/or into a chamber of a dialyser, at least a first and a second filtration station 16, 17 placed along the said fluid path, the second filtration station operating downstream of the first filtration station, the said method comprising the phases of:
  a) placing a filter 18, 19 in correspondence with each station 16, 17;
  b) sending liquid along the said fluid path 12 through the said first and the said second filtration stations 16, 17 towards the said injection region;
  c) removing the filter 18 which operates in correspondence with the first filtration station 16;
  d) placing, in correspondence with the first station 16, the filter 19 which operates in correspondence with the second filtration station; and
  e) placing a new filter in correspondence with the second station 19, and
- a device for in-line preparation of liquid, in particular for producing a method according to the invention, the said device comprising:
  a fluid path 12 from a liquid source to a region 14 for injecting the said liquid into an extracorporeal blood circuit and/or into the cardiovascular system of a patient and/or into a chamber of a dialyser;
  means 15 for determining movement of the liquid along the said path;
  at least a first and a second filtration station 16 and 17 placed along the said fluid path, the second filtration station operating downstream of the said first filtration station;
  a filter 18, 19 operating in correspondence with each filtration station;
  a transfer unit 26 acting at least on the filter which operates in correspondence with the said second station in order to transfer this filter from the said second station to the said first station.

BRIEF DESCRIPTION OF THE DRAWINGS

Other characteristics and advantages will become more apparent on reading the detailed description of a preferred but non-exclusive embodiment of a method and of a device for the in-line preparation of liquid, and an apparatus for extracorporeal blood treatment which uses the said method and the said device according to the present invention.

This description will be given below with reference to the appended figures, given solely by way of non-limiting indication, in which.

DETAILED DESCRIPTION

Figure 1A:
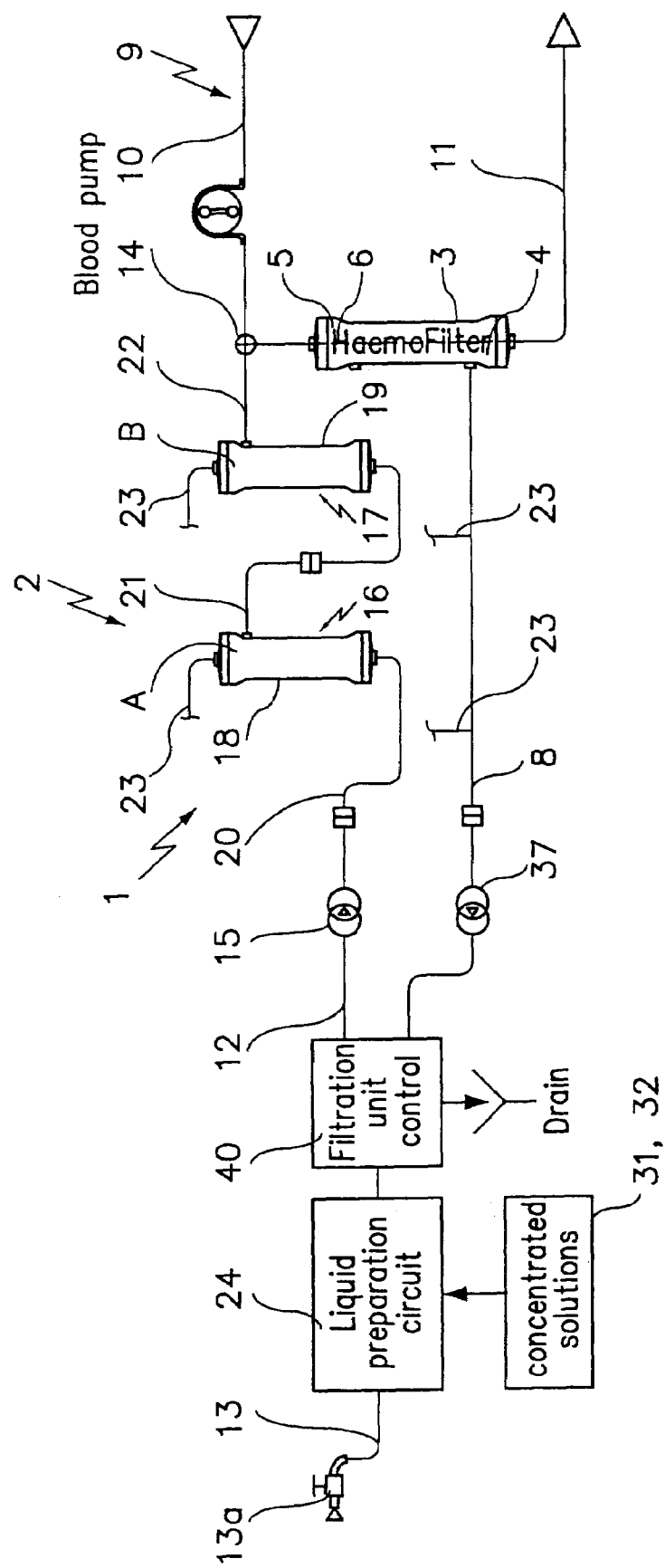
FIGS. 1A, 1B, 1C show schematically a haemofiltration apparatus capable of using the method and the device according to the invention.
Figure 1B:
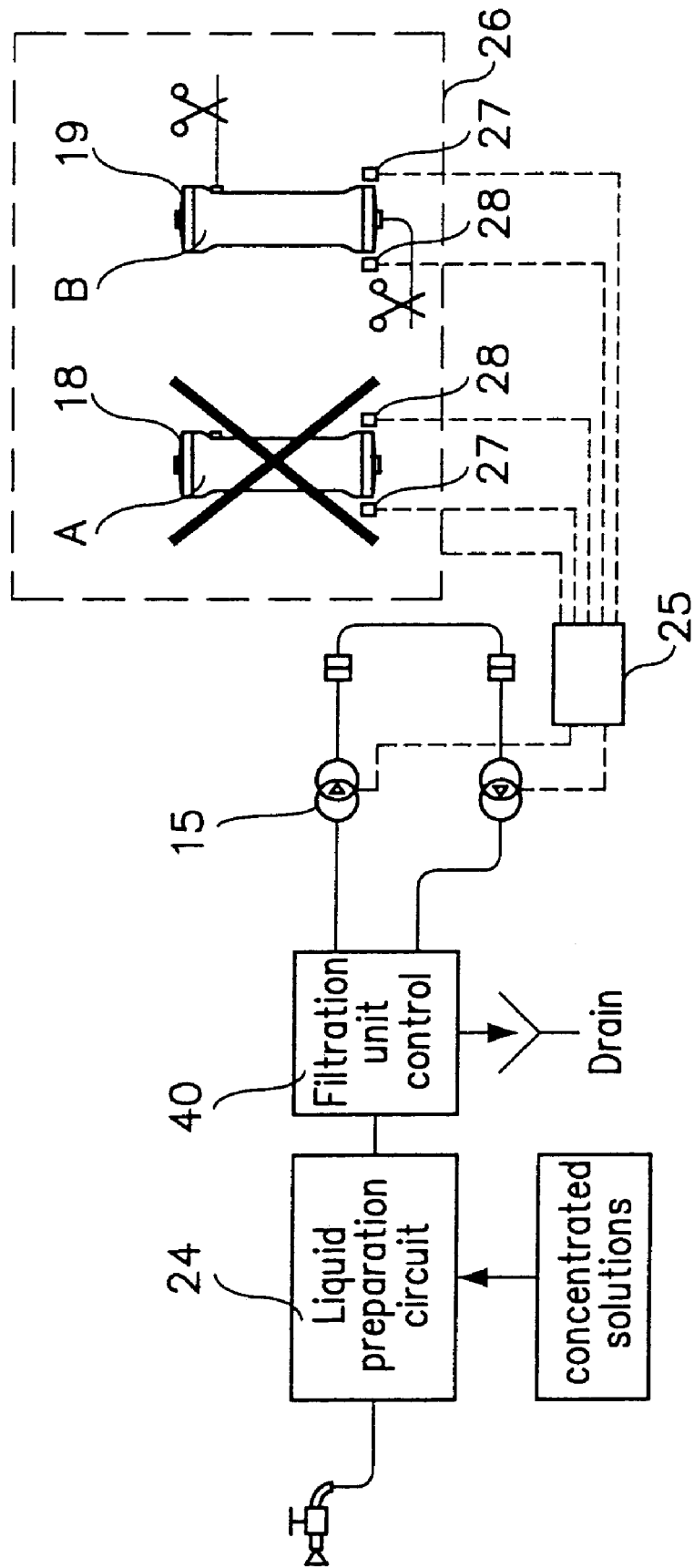
Figure 1C:
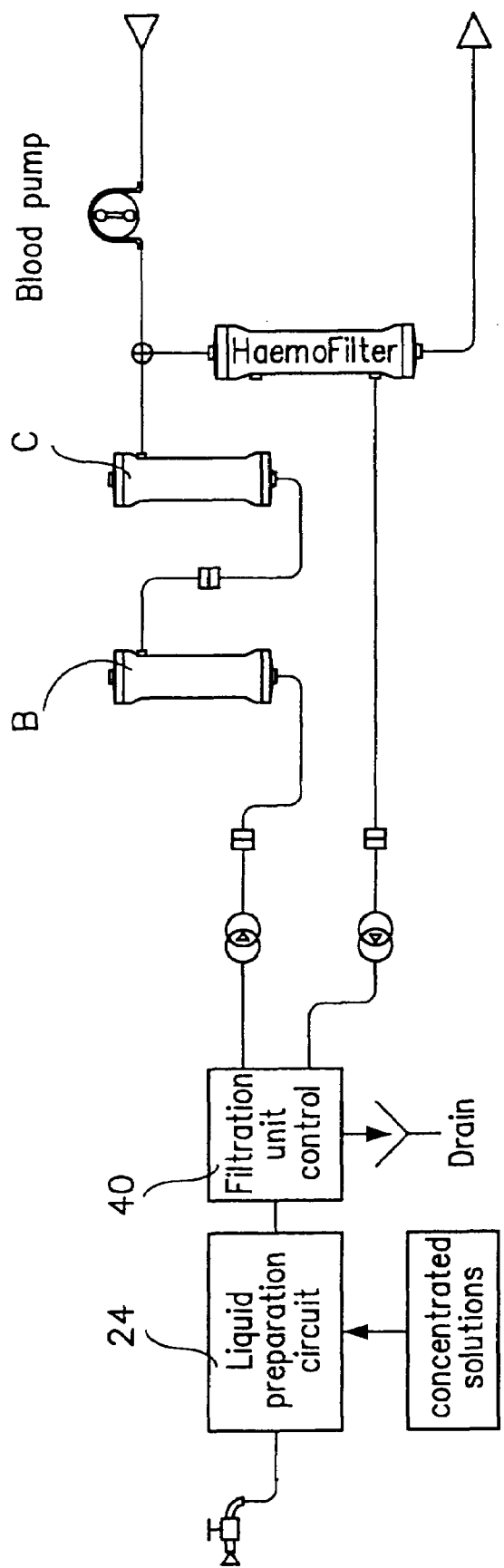
Figure 2:
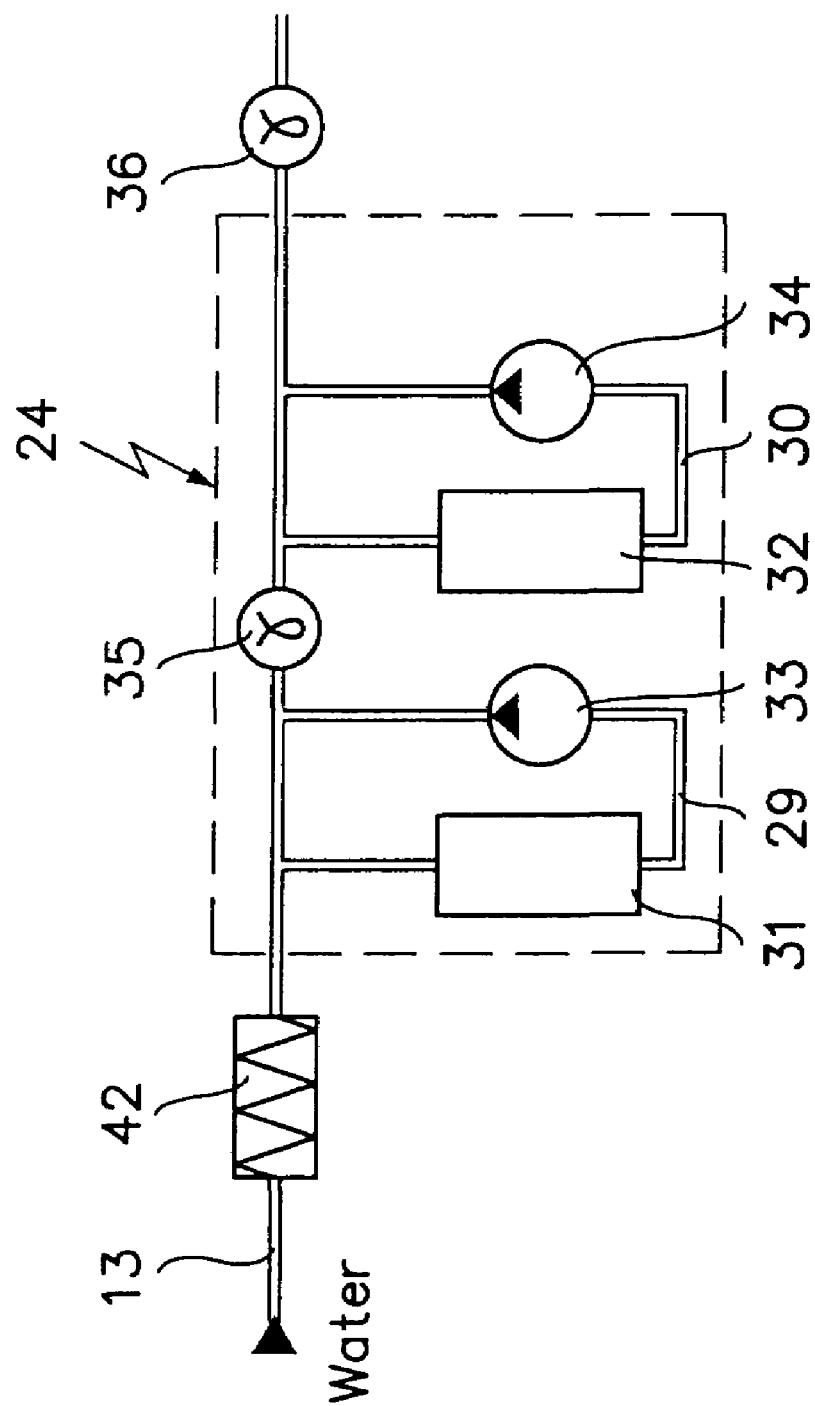
FIG. 2 shows part of the apparatus according to FIGS. 1A, 1B, 1C, relating to the circuit for preparing the liquid.

With reference to the appended figures, an apparatus for extracorporeal blood treatment is denoted overall by 1. The apparatus 1 represented in FIGS. 1A and 1C is in a functional configuration which allows it to carry out a haemofiltration treatment. In any case, it will be noted that this configuration is given purely by way of example and that the present invention may obviously find use in any extracorporeal blood treatment (for example, haemodialysis, haemofiltration, haemodiafiltration) where it proves to be necessary or convenient to produce a sterile liquid in line. The invention may be used to produce a dialysis liquid and/or a liquid for injecting into an extracorporeal blood circuit and/or a liquid for direct injection into the cardiovascular system of a patient. The apparatus 1 comprises at least one device for the in-line preparation of liquid, denoted overall by 2 and again described in detail further on, and at least one blood treatment unit 3. The unit 3 has a first chamber 4 and a second chamber 5 which are separated by at least one semipermeable membrane 6; the first chamber comprises an outlet opening which may be connected to a discharge line 8, while the second chamber 5 may be connected to an extracorporeal blood circuit 9 having at least one branch 10 which takes the blood from the patient and at least one branch 11 for restoring the blood to the patient. The in-line liquid preparation device 2 comprises a fluid path 12 which extends from one upstream end 13 which may be connected to a mains water supply 13a, up to a region 14 for injecting liquid into the extracorporeal blood circuit and/or directly into the cardiovascular system of a patient. The line 12 may be connected to the first chamber 4 in the in-line preparation of the dialysis liquid. In the example shown, the injection region 14 is placed in correspondence with the extracorporeal circuit 9 and in particular on the branch 10 for taking blood from the patient, upstream of the unit 3 (predilution). Similarly, the injection region may be provided in correspondence with the branch 11 (post-dilution) or with both branches 10 and 11 (simultaneous predilution and postdilution). Means, which for example comprise a pump 15, operate along the fluid path 12 in order to transfer the liquid towards the injection region 14. The device 2 further comprises at least a first and a second filtration station 16 and 17 placed along the fluid path 12; as shown in the appended figure, the second filtration station 17 is placed downstream of the first filtration station 16 in the direction of flow of the liquid along the path 12; a respective filter 18, 19 operates in correspondence with each of the filtration stations. Conventional valve means (not shown) may, as desired, bring each filter 18, 19 from an operating situation in which the filter is placed in flow communication with the fluid path to a non-operating situation in which the filter is hydraulically isolated from the fluid path, and conversely. To go into more detail, it will be specified that each of the filters 18, 19 (structurally identical to each other) comprise at least a first chamber and a second chamber separated by a filtration membrane, at least one opening for access to the said first chamber and at least one outlet opening of the said second chamber. In its turn, the fluid path 12 has a first part 20 capable of connecting the liquid source to the first chamber of the filter 18 which operates in the said first station, a second part 21 capable of connecting the second chamber of the filter 18 which operates in the said first station to the first chamber of the filter 19 which operates in the said second station, and a third part 22 capable of connecting the second chamber of the filter 19 which operates in the said second station to the said injection region 14. In this way, the liquid which reaches the injection region 14 has necessarily passed through both the filter 18 and the filter 19.

Each filter also has an outlet opening in correspondence with the said first chamber, in order to transfer the fluid from the said first chamber of the filter, tangential to the filtration membrane. For this purpose, the filter outlet openings may be connected to the discharge line 8 or to independent discharges, by means of pipes 23 on which flow adjustment members act, controlled by a control unit 25 (FIG. 1B). The flow regulation members may, for example, comprise a valve and/or a pump which operates on each of the said pipes 23. The control unit 25 may control the regulation members in order to carry out tangential washing of the first chamber, continuously or at successive time intervals. It will be noted that in correspondence with each station, provision can also be made for a recirculation line (not shown) capable of sending at least part of the liquid discharged through the outlet opening of the first said chamber to the inlet opening.

A transfer unit 26 acting on the filter 18 and 19 is capable of bringing the filter operating in the first station to a discharge station and of transferring the filter present in the second station to the said first station. The control unit 25 coordinates the actuation of the transfer unit by actuating means 15. In practice, during a liquid preparation session, which corresponds to a patient treatment phase, the unit 25 controls the means 15 by causing a flow of liquid over a suitable range along the path 12; when the liquid preparation session is finished, the unit 25 proceeds to actuate the transfer unit 26 in order to bring the filter operating in the first station into the outlet station and in order to bring the filter present in the second station into the first station.

It will be noted that the sensors 27 for indicating the presence of a filter in each station and for sending a corresponding signal to the control unit 25 operate in correspondence with the first and with the second station; each filter may also be given an identification code which may be read by suitable detectors 28 (for example, optical, electrical, magnetic or electromagnetic detectors capable in all cases of receiving information carried by the filter) which operate in correspondence with each station and capable of emitting a respective identification signal to the control unit 25.

The unit 25 may be programmed to allow the in-line preparation of liquid and the sensors 27 indicate that the respective filters are effectively fitted into the stations. Furthermore, by virtue of the possibility of identifying the identity of each filter, the unit 25 may be programmed so as to allow the in-line preparation of liquid only if a filter (filter B in FIG. 1B) which has only been used for a single previous session (or a new filter—filter A in FIG. 1A) is used in the first station and if a new filter (filter B in FIG. 1A; filter C in FIG. 1C) is used in the second station. Where the conditions mentioned above are not complied with, the unit 25 may be programmed to emit an alarm signal and/or to interrupt giving treatment at parts of the apparatus 1.

Finally, in relation to the specific embodiment shown, the device 2 further comprises a preparation circuit 24 having a heating member 42 which operates downstream of the end 13, and at least two bypass channels 29, 30 which follow each other along the path 2. A cartridge or a container 31, 32 for concentrated solutions (for example just one) and a pump 33, 34 operate on each bypass channel. Concentration or conductivity sensors 35, 36 are placed along the path 2, downstream of the region involved for each channel, so as to send corresponding signals to the unit 25. On comparing the values identified by the sensors to reference values, the unit 25 may adjust the range of the pump to each auxiliary channel in a suitable manner. A discharge pump 37, downstream of which a flow meter operates, may be provided along the discharge tube 8. Another flow meter is also provided in correspondence with the path 12, upstream of the pump 15. The flow meters are part of a circuit for controlling the ultrafiltration 40. By virtue of the signals coming from the flow meters and by virtue of suitable control of all the pumps described above, it is possible to manage the ultrafiltration and therefore the weight loss of the patient, in a suitable manner.

In use, the device 2 described is suitable for implementing a method which is also part of the present invention and which comprises the phases described below. On activating the device 2 for the first time, the fitting of a new and sterile filter is carried out, in correspondence with each station; next, at the same time as the extracorporeal treatment is executed, the means 15 are actuated to send liquid along the said fluid path 12, through the filtration stations and the filters 18, 19, towards the injection region 14. When the treatment or the passing-through has lasted for some time (which is possibly programmable), the filter which operates in correspondence with the first filtration station is removed and the filter present in the said second station is isolated from the fluid path 12; finally, a procedure for cleaning and disinfecting the fluid path 12 and, if necessary, the various pipes of the apparatus 1 is carried out without the filters 18, 19 being involved in this operation (FIG. 1B). It will be noted that it is not necessary to disinfect the filter 19 present in the second station. When a new treatment has to be carried out, the filter present in correspondence with the second filtration station is placed in the first filter station and a new sterile filter is placed in the second station; next, the device is ready for a new session, at the end of which the filter is removed from the first station and it is replaced by the one present in the second station, as has already been described above. If the phases of removing and replacing filters had to be carried out periodically and not at the end of each treatment, before removing filters from respective stations, the flow of liquid along the path 2 will in any case be interrupted.

The invention has important advantages.

Firstly, the sterility of the liquid downstream of the second filtration station is guaranteed since the downstream filter is always new and sterile. Furthermore, it will be found that the filter most affected by the presence of any undesirable particles in the filter is the upstream filter which fulfils its function for a single cycle and which is therefore replaced with no risk that bacteria or pyrogenic agents are spread following ineffective disinfection. Furthermore, since there are no disinfection actions, the used filters cannot be damaged or lead to propagation of undesirable agents. The entire apparatus is obtained with extreme simplicity, since the filters used are identical, with additional advantages in terms of management.

The invention claimed is:

1. A method for in-line preparation of liquid for an extracorporeal blood treatment apparatus, which apparatus comprises at least one fluid path from a liquid source to a region for injecting said liquid into an extracorporeal blood circuit and/or into a cardiovascular system of a patient and/or into a chamber of a dialyser, at least a first and a second filtration station placed along said fluid path, the second filtration station operating downstream of the first filtration station, said method comprising the steps of:
   a) placing a filter in correspondence with each station;
   b) sending liquid along said fluid path through said first and said second filtration stations towards said injection region;
   c) removing the filter which operates in correspondence with the first filtration station;
   d) placing, in correspondence with the first filtration station, the filter which operates in correspondence with the second filtration station; and
   e) placing a new filter in correspondence with the second filtration station.

2. A method according to claim 1, wherein the steps a), b), c), d), and e) follow one another over time.

3. A method according to claim 1, wherein after said step of placing a new filter, provision is made to repeat the steps b), c), d), and e) in succession one after another.

4. A method according to claim 1, wherein each step b) during which the fluid liquid is sent to said injection region corresponds to the administration of an extracorporeal treatment to a patient by said apparatus, the steps c), d), and e) are carried out once the extracorporeal treatment is finished.

5. A method according to claim 1, wherein each step b) during which the liquid is sent to said injection region corresponds to a predetermined interval of time.

6. A method according to claim 1, wherein each step b) during which the liquid is sent to said injection region corresponds to an interval of time that can be programmed by a user.

7. A method according to claim 2, wherein between said steps b) and c), a step of interrupting the flow of liquid along said fluid path is provided.

8. A method according to claim 2, wherein between said steps c) and d), the following sub-steps are provided:
   isolating the filter of said second filtration station from liquid in said fluid path; and
   carrying out an operation of disinfecting said fluid path without acting on the filter present in said second filtration station.

9. A method according to claim 1, wherein the filters operating in said first and in said second filtration station are structurally identical to each other.

10. A method according to claim 1, wherein a sterile filter is placed in correspondence with said second filtration station, in order to define a barrier capable of guaranteeing the sterility of the liquid downstream of said second filtration station, in use.

11. A method according to claim 1, wherein each one of said filters comprises at least a first and a second chamber separated from each other by a filtration membrane, at least one opening for access to said first chamber and at least one outlet opening of said second chamber.

12. A method according to claim 11, wherein said fluid path comprises:

a first part arranged to connect the liquid source to the first chamber of the filter which operates in said first filtration station, a second part arranged to connect the second chamber of the filter operating in said first filtration station to the first filter chamber operating in said second filtration station, and a third part arranged to connect the second chamber of the filter operating in said second filtration station with said injection region.

13. A method according to claim 11, wherein each filter also comprises an outlet opening in correspondence with said first chamber, in order to provide a step of transferring fluid in said first chamber of the filter tangentially to the filtration membrane.

14. A method according to claim 13, wherein said step of transferring fluid tangentially is carried out periodically.

15. A method according to claim 13, wherein said step of transferring fluid tangentially is carried out continuously.

* * * * *